(12) United States Patent
Benjamin

(10) Patent No.: US 6,357,282 B1
(45) Date of Patent: Mar. 19, 2002

(54) TENNIS BALL TESTER

(76) Inventor: Robert E. Benjamin, 75 Lakewood Ave., Cedar Grove, NJ (US) 07009

( * ) Notice: Subject to any disclaimer, the term of this patent is extended or adjusted under 35 U.S.C. 154(b) by 0 days.

(21) Appl. No.: 09/690,706

(22) Filed: Oct. 18, 2000

(51) Int. Cl.[7] .................................................. G01N 3/24
(52) U.S. Cl. ............................................. 73/81; 73/818
(58) Field of Search ................................ 73/78, 81, 82, 73/83, 85, 818, 824, 788

(56) References Cited

U.S. PATENT DOCUMENTS

| | | | | |
|---|---|---|---|---|
| 4,154,095 A | * | 5/1979 | Snyder ........................... | 73/78 |
| 4,509,362 A | * | 4/1985 | Lyons ............................. | 73/79 |
| 5,222,391 A | * | 6/1993 | Reenstra ........................ | 73/81 |
| 5,291,774 A | * | 3/1994 | Putnam, Jr. ................... | 73/82 |
| 5,511,410 A | * | 4/1996 | Sherts ........................... | 73/81 |
| 5,567,870 A | * | 10/1996 | Harris ........................... | 73/81 |
| 5,639,969 A | * | 6/1997 | D'Adamo ...................... | 73/81 |
| 5,760,312 A | * | 6/1998 | Mackay et al. ................ | 73/81 |
| 5,837,889 A | * | 11/1998 | Slenker ......................... | 73/81 |

\* cited by examiner

*Primary Examiner*—Max Noori
(74) *Attorney, Agent, or Firm*—Alfred C. Hill

(57) ABSTRACT

A portable and manually operated lightweight tennis ball tester with a housing for receiving at least one tennis ball to be tested; a pair of bars disposed in the housing in a substantially parallel relationship, each of the pair of bars being disposed in opposite sides of the at least one tennis ball; force applying system coupled to one of the pair of bars and extending out of one end of the housing to enable applying a force to the at least one tennis ball; and gauge device coupled to the other of the pair of bars to provide an indication of whether the at least one tennis ball meets standard of play established by the United States Tennis Association.

20 Claims, 3 Drawing Sheets

TENNIS BALL TESTER

BACKGROUND OF THE INVENTION

The present invention relates to tennis ball testers and more particularly to a portable and manually operated lightweight tennis ball tester.

The primary purpose of a tennis ball tester is to check the quality of a tennis ball to see if it meets the standards required for play established by the United States Tennis Association. There are large elaborate and expensive machines used by the tennis ball manufacturers to test their newly produced balls. Two leading tennis ball manufacturers have suggested that an acceptable field test is to drop the ball from a height of 100 inches (8 feet, 4 inches) onto a hard surface. The tennis ball must bounce 53 inches to be considered good. This is an impractical test to perform on a tennis court because of the height and the weather factors. Tests show it takes a considerable amount of pressure to compress a tennis ball to a point where an accurate dependable reading can be obtained to determine if the ball meets the requirements for play. The following ate objective of a tennis ball tester.

1. The tester should be lightweight and portable.

2. The testing of the tennis ball should be quick easy and reliable.

3. The tester must be capable of being carried in a tennis bag and will receive some abuse so it should be durable.

4. A reasonably priced tester is a very important feature of the tester that all other testers lack. The cost of a container of three balls is approximately $2.00. We must approach the tennis ball tester with common sense. The market is limited to the more serious players and those who may purchase it as a gift. Why buy an expensive tester when one can purchase a new container of balls for $2.00. This narrow market and the low cost of new balls make it a risky adventure for an investor. Therefore, the tennis ball tester must be inexpensive. At present there isn't a tennis ball tester on the market because of impractical design and prohibitive manufacturing costs of the prior art. The prior art found in a search is found to be defective in most or all of the conditions essential to a practical low price tennis ball tester outlined hereinabove that would appeal to the limited market available.

U.S. Pat. No. 5,639,969 by the Adamo presents several problems that make it impractical. The device of this patent requires a great amount of force to compress a tennis ball to a size that an accurate reading of its condition may be taken. In this device pressure must be applied directly to the ball without benefit of any mechanical advantage. In the Adamo device one must overcome the spring to squeeze the ball through a small angular ring. The weaker player will find it difficult, if not impossible, to force the ball through the ring. In this device, the player must select one of the three gauges to determined the condition of the balls' Knapp. There are very small difference in a tennis ball's Knapp. When any testing device relies on an opinion, the accuracy of the device must be questioned.

U.S. Pat. No. 5,837,889 to Slenker measures the pressure difference between balls. But it fails to identify the balls with the proper pressure to meet the standard of play. If a used ball has less pressure than a new ball it still may meet the pressure requirement, or play requirement. The scale on this device does not have a marker line to indicate a ball has adequate pressure for play. It is not sound engineering to expect an accurate reading from a cork friction pad that is hand tightened by a wing screw to calibrate the gauge. Tightness is dependent on each individual hand. The flexible arm which must bow over an 8 inch span can also lead to inaccurate and inconsistent readings. Aside from all the engineering and mechanical defects a considerable investment must be made in tooling, molds and machining of the Slenker device. As mentioned earlier, tennis ball testers have a limited market and these tooling costs would deter any investor.

U.S. Pat. No. 5,567,870 to Harris fails to solve the tennis ball testing problem in several areas. Testing has shown that to get an accurate reading on a tennis ball it must be compressed or indented close to approximately halt its diameter. The Harris device does not penetrate the ball with sufficient depth to get readings which would be accurate and consistent. A great amount of pressure is required to probe deeply into the ball. This requires a torsion spring of considerable torque to force the plunger to an adequate depth. This demands a great amount of hand grip strength which the average person does not have. As state above, the plunger must penetrate deeply into the ball. This is not accomplished by the Harris device. The length of travel of the plunger requires a special type of pressure gauge. The pressure gauge shown is not available as a standard off the shelf item. A special gauge is required to meet these specifications. An unworkable mechanics combined with the high cost of special tooling, molds and a custom made gauge make the Harris device an unsound venture to pursue for an investor.

U.S. Pat. No. 5,511,410 to Sherts discloses a gear rack pinion and spring as his basic components. In this embodiment there is no mechanical advantage to the operator inserting the ball. A very strong spring must be employed to probe deeply into the ball for an accurate reading of its pressure. The operator must overcome the spring tension. You are also inserting the ball in a vertical plane while the sensing stem must react in a horizontal plane. This results in great pressure required in inserting the ball and more resistance on the lower bearing surface of the sensing stem.

The Sherts patent offers alternate designs, but they all lack the mechanical advantage required as well as other shortcomings. It is claimed in this patent that the ball tester can be for other types, such as golf balls. Balls for other sports are radically different. To accommodate other balls in this device is impractical and lessens the accuracy of the unit. Sherts device as well as the other embodiments does not establish a minimum standard for a ball playability. A new ball is used as a standard which means that any ball that fails to match the new ball fails the test. A ball still may meet the standard after hours of use. The cost to produce Sherts devices is prohibitive. The special gear rack and pinion must be made along with a special enclosure. This calls for special tooling and the cost is not justified by the limited market.

U.S. Pat. No. 5,291,774 to Puckman Jr. discloses a tester that determines the playability of a tennis ball by the amount the ball is compressed by a 6 pound weighted arm. As stated earlier, in reviewing previous patents a tennis ball is a highly pressurized sphere. A 6 pound weight would not compress the ball to a degree that can be accurately read even at 5 times the length of the compression arm. The 6 pound weight of the arm combined with the additional components make it too heavy to be a portable tester. It is stated in the Puckman patent in column 2, line 5 that the placement of the scale "play zone" is for a new ball and the rest of the scale may be arbitrarily used depending on the level of play. It can only be assumed that the players may set their own standard for the playability of a ball. This poses the question of why have a ball tester if it is not going to identify a used ball that still qualifies to meet the United States Tennis Associations standard.

U.S. Pat. No. 5,222,391 to Reenstra introduces a complex electronic device. This gauge is too sophisticated for the task of testing the ball. It consists of an electronic system with a delicate electronic pressure sensitive sensor plate. This is to detect small changes in the ball size under pressure, Carrying this unit in a tennis bag will subject the unit to vibration, heat on a tennis court and grit on the clay courts. The electronic and sensor plates are critical elements of this approach and its dependability and accuracy are in question. There seems to be no method of calibrating this gauge by the tennis layman. The requirements of a battery add to its weight and maintenance problem. Failure of one of the many electronic components present a problem to a player. In a mechanical tester, it is much easier to detect a failed part than in a complex electronic device. This unit would be costly to produce for the available market.

SUMMARY OF THE INVENTION

An object of the present invention is to provide an improved portable and manually operated lightweight tennis ball tester overcoming the disadvantages of the above sited prior art tennis ball testers.

Another object of the present invention is to provide a tennis ball tester that is lightweight, portable, easy to use, reliable and that may be carried in a tennis bag which requires durability.

Still another object of the present invention is to provide a portable and manually operated lightweight tennis ball tester that is reasonably priced.

The basic design of the tennis ball tester disclosed herein lends itself to simple fabrication which can be accomplished in a sheet metal shop. There is no expensive tooling dyes, castings or molds required to produce this unit.

A further object of the present invention is to provide an inexpensive tennis ball tester that would be a sound venture for an investor to pursue.

Still a further of the present invention is to provide a tennis ball tester that has a highly leveraged toggle system which when closed activates the tester to indicate the ball condition on a gauge.

A feature of the present invention is a portable and manually operated lightweight tennis ball tester comprising a housing for receiving at least one tennis ball to be tested, a pair of bars disposed in the housing in a substantially parallel relationship, each of the pair of bars being disposed on opposite sides of the at least one tennis ball; force applying means coupled to one of the parallel bars and extending out of one end of the housing to enable applying a force to the at least one tennis ball; and gauge means coupled to the other of the pair of bars to provide an indication of whether the at least one tennis ball meets the standard of play established by the United States Tennis Association.

BRIEF DESCRIPTION OF THE DRAWING

Above-mentioned and other features and objects of the present invention will become more apparent by reference to the following description taken in conjunction with the accompanying drawings in which.

DESCRIPTION OF THE PREFERRED EMBODIMENTS

The tennis ball tester in accordance with the principles of the present invention is used to determine if a used tennis ball has sufficient pressure to meet the standard of play established by the United States Tennis Association. This is an important consideration with serious tennis players and tennis instructors. The tennis ball must rebound and react when struck to established standards. A ball not meeting these standards will not rebound properly and will require a great deal of more power to drive the ball over the net. This distorted bounce and extra power required upsets a players rhythm and timing.

Figure 1:
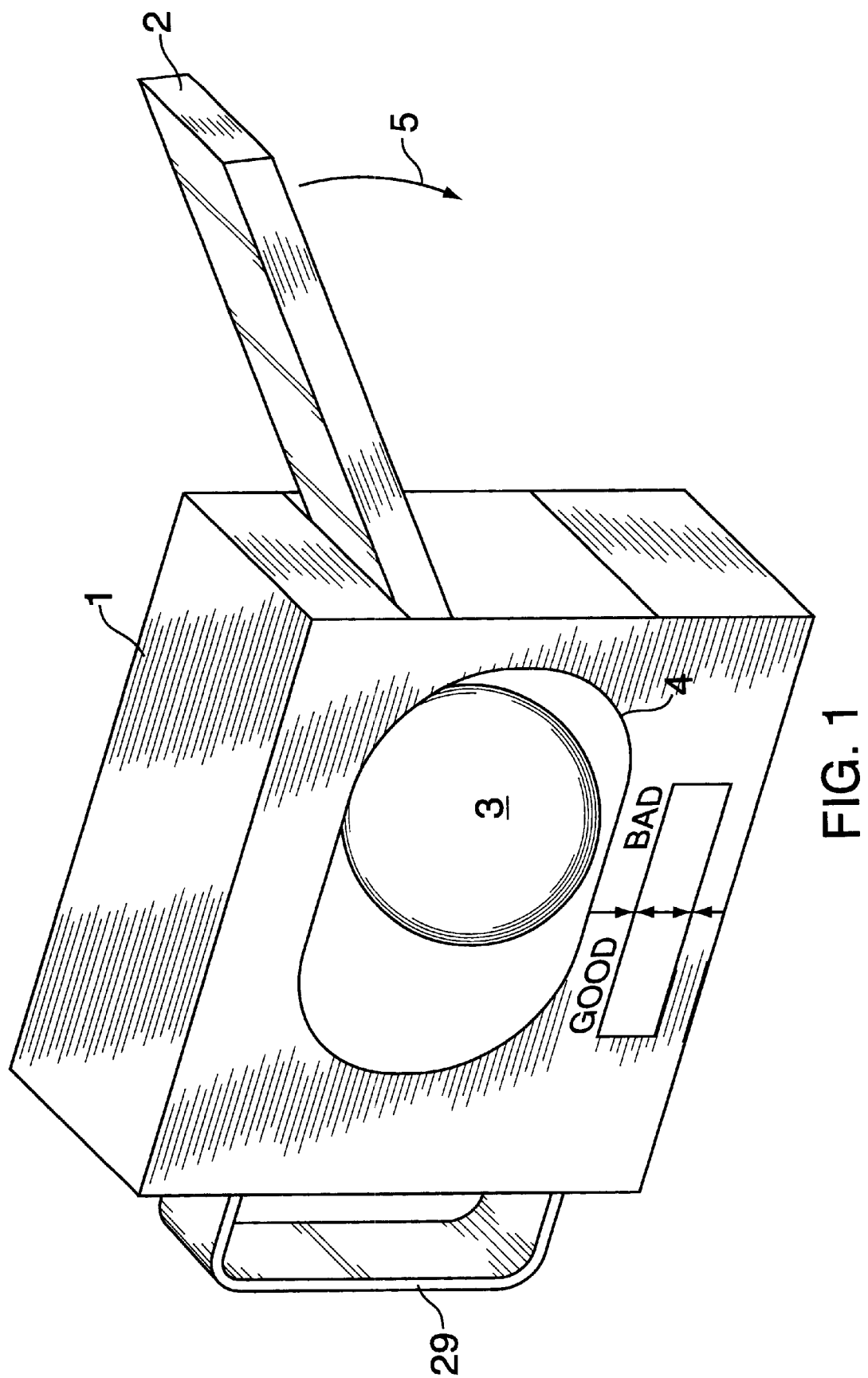
FIG. 1 is a perspective view of one embodiment of the tennis ball tester in accordance with the principles of the present invention.
Figure 2:
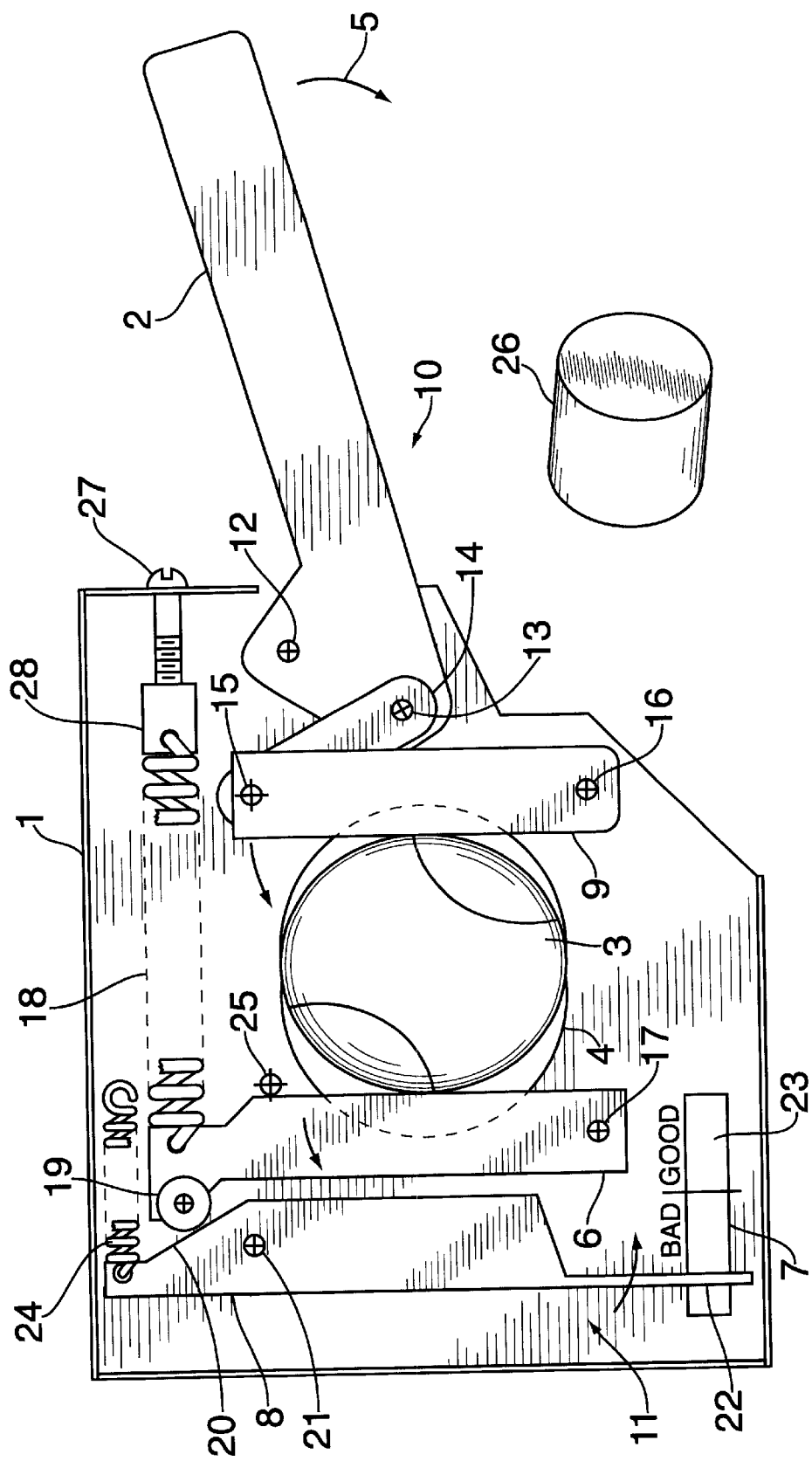
FIG. 2 is a front view of the tennis ball tester of FIG. 1 with the front cover removed in accordance with the principles of the present invention.

Referring to FIGS. 1 and 2, the tester, in accordance with the principles of the present invention, includes an aluminum case or housing 1 which is 1½ inches thick by 6 inches wide by 7 inches long with a hand grip or member 2 projecting one end of housing 1. The ball 3 to be tested is placed in an obround opening 4. The hand grip or member 2 is then pushed downward in the direction of arrow 5 and locks in place. This sets in motion a highly leveraged toggle action which compresses ball 3 against a spring loaded arm or bar 6, arm 6 in turn activates an indicator 7 to display the condition of ball 3. The higher the ball's pressure the more the arm 6 moves the indicator arm 8 to ascertain the condition of ball 3.

The word "obround" referred to hereinabove with regard to the opening 4 refers to the terminology used by machinists where the hole is not actually oval, or round, but rather is an opening that has two ends curved as shown in FIG. 1 with a straight line connection between the curves.

Figure 3:
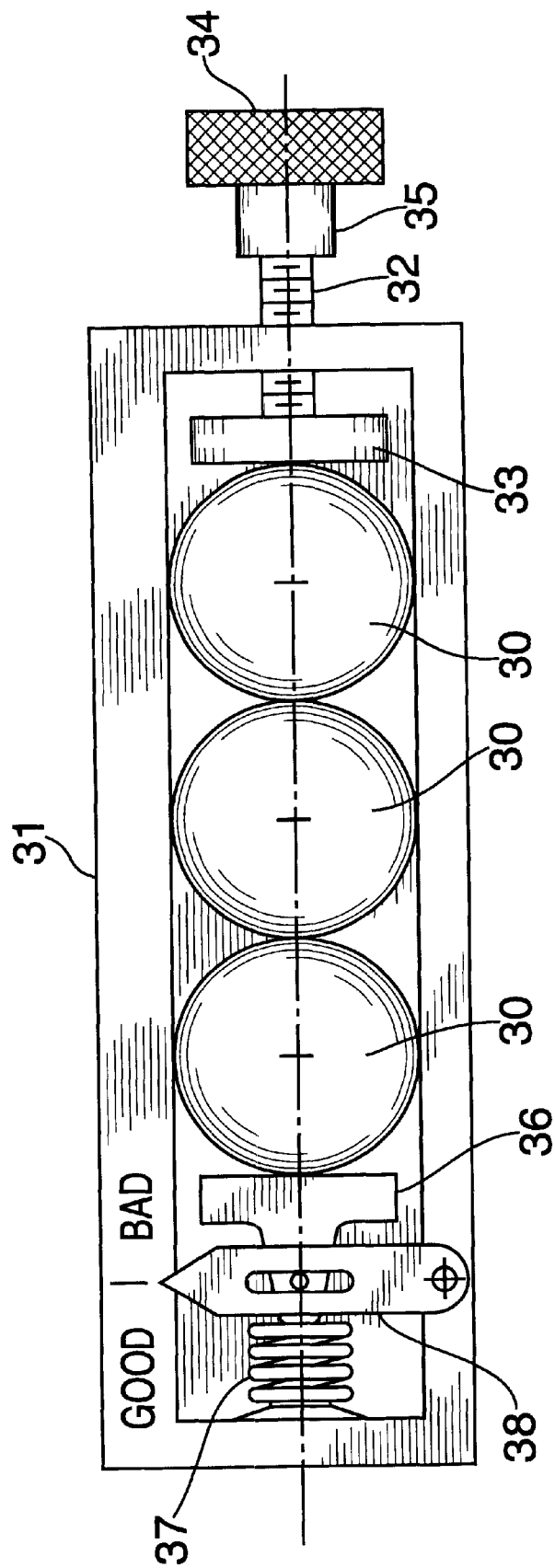
FIG. 3 is a schematic illustration of a second embodiment of the tennis ball tester in accordance with the principles of the present invention.

As shown in FIG. 2 particularly, the housing 1 receives one tennis ball to be tested but it is possible that more than one tennis ball could be tested by an embodiment that is disclosed in FIG. 3. In the embodiment of FIG. 2, the pair of bars 6 and 9 are disposed in a substantially parallel relationship in housing 1 with each of the bars being disposed on opposite sides of the tennis ball 3. Force applying means 10 is coupled to one of the bars, such a bar 9, with the member or arm 2 extending out one end of housing 1 to enable applying a force to the tennis ball 3. A gauge means 11 coupled to the other of the pair of bars, such as bar 6, provides an indication at gauge 7 whether the tennis ball meets standards of play established by the United States Tennis Association.

In operation, the tennis ball 3 is inserted into the obround hole 4 of the tennis housing 1. The member 2 or handgrip is depressed rotating clockwise in the direction of arrow 5 around the fixed pivot point 12 causing the pivot points 13 to move link 14. Link 14 pushes against pivot point, or pin 15 causing the bar 9 to rotate around the pivot point 16. This toggle action locks the pressure arm 9 in place. The ball 3 being compressed forces its internal pressure to react against the anvil arm or bar 6 which rotates around fixed pin or pivot 17. The main spring 18 is hooked onto the bar 6 which resists the internal pressure of the ball 3. The greater the internal pressure of ball 3 the more arm or bar 6 rotates around the pivot 17. The roller 19 presses against the bevel surface 20 of indicator arm 8 which rotates around fixed pin or pivot 21. The indicator arm pointer 22 moves in the window 23 of gauge 7 to indicate the condition of the ball 3, bad or good. The indicator arm spring 24 keeps the bevel 20 in contact with roller 19 while the ball 3 is locked in place.

To release the ball 3, hand grip or member 2 is lifted counterclockwise unlocking and releasing the pressure on the ball 3. The anvil arm or bar 6 returns to its original position resting against stop 25.

To calibrate the tester in accordance with the principles of the present invention a test rod 26 is inserted in the obround hole 4 and locked in place by pressing the hand grip or member 2. Screw 27 is turned moving screw eye 28 until the indicator arm pointer 22 lines up between the good and bad regions in the window 23 of gauge 7.

As illustrated in FIG. 1, a secondary or auxiliary handle 29 is provided and can be incorporated in the embodiment of the tester shown in FIG. 2 to assist in holding the tennis ball tester while testing the tennis ball 3.

Referring to FIG. 3 there is illustrated therein an embodiment of the tennis ball tester in accordance with the principles of the present invention in which it is possible to test three tennis balls. The tennis balls 30 are placed in a housing 31 having a threaded stud 32 extending out of housing 31 at one end thereof. The stud 32 operates a bar 33 to apply a force to the tennis balls 30. The knob 34 fastened to stud 32 is turned clockwise until the shoulder 35 sits against the housing 31. The amount of pressure in the balls 30 determines the distance the plate or bar 36 moves against spring 37. If the balls 30 have proper pressure, the bar 36 moves arrow arm 38 to indicate balls 30 are good.

By adjusting the arrow arm 38 and the bar 36, the unit can be used to test one or two balls rather than three as illustrated.

While I have described above the principles of my invention in connection with specific apparatus, it is to be clearly understood that this description is made only by way of example and not as a limitation to the scope of my invention as set forth in the objects thereof and in the accompanying claims.

I claim:

1. A portable and manually operated light weight tennis ball tester comprising:

a housing for receiving at least one tennis ball to be tested;

a pair of bars disposed in said housing in a substantially, parallel relationship, each of said pair of bars being disposed on opposite sides of said at least one tennis ball;

force applying means coupled to one of said pair of bars and extending out of one end of said housing to enable applying a force to said at least one tennis ball; and gauge means coupled to the other of said pair of bars to provide an indication of whether said at least one tennis ball meets standard for play established by the United States Tennis Association.

2. A tennis ball tester according to claim 1, wherein said force applying means includes a member extending out of said housing to initiate the application of said force to said one of said pair of bars, and a highly leveraged toggle system coupled between said member and said one of said pair of bars to apply said force to said one of said pair of bars and, hence, said at least one tennis ball.

3. A tennis ball tester according to claim 2, wherein said member includes a first pivot point within and fastened to said housing; and said highly leveraged toggle system includes a first link having one end pivoted to said member at a second pivot point space from said first pivot point, and the other end pivoted at a third pivot point disposed at one end of said one of said pair of bars, the other end of said one of said pair of bars being pivoted at a fourth point fastened to said housing.

4. A tennis ball tester according to claim 3, wherein said gauge means includes a first spring connected to one end of said other of said pair of bars, a fifth pivot point fastened to said housing and pivoted to the other end of said other of said pair of bars, a gauge disposed in said housing to be seen externally thereof to indicated whether said at least one tennis ball meets said standard of play, an indicator arm coupled to said other of said pair of bars and said gauge, said indicator arm being pivoted on a sixth pivot point fastened to said housing adjacent said one end of said other of said pair of bars, and a second spring fastened to an end of said indicator arm remote from said gauge and spaced from said sixth pivot point adjacent said one end of said other of said pair of bars.

5. A tennis ball tester according to claim 4, further including tension adjusting means coupled to said first spring.

6. A tennis ball tester according to claim 5, wherein said tension adjusting means includes a tension adjusting screw extending through said housing for an adjustable connection to an end of said first spring remote from said one end of said other of said pair of bars.

7. A tennis ball tester according to claim 6, further including a roller connected to said one end of said other of said pair of bars adjacent said first spring engaging an inclined surface of said indicator arm between said second spring and said sixth pivot point to move said indicator arm in response to movement of said other of said pair of bars.

8. A tennis ball tester according to claim 7, further including a stop pin fastened to said housing adjacent said one end of said other of said pair of bars spaced from said first spring.

9. A tennis ball tester according to claim 8, wherein said member provides a handle for said tennis ball tester.

10. A tennis ball tester according to claim 9, further including a second handle fastened to said housing opposite said member.

11. A tennis ball tester according to claim 1, wherein said gauge means includes a first spring connected to one end of said other of said pair of bars, a first pivot point fastened to said housing and pivoted to the other end of said other of said pair of bars, a gauge disposed in said housing to be seen externally thereof to indicated whether said at least one tennis ball meets said standard of play, an indicator arm coupled to said other of said pair of bars and said gauge, said indicator arm being pivoted on a second pivot point fastened to said housing adjacent said one end of said other of said pair of bars, and a second spring fastened to an end of said indicator arm remote from said gauge and spaced from said second pivot point adjacent said one end of said other of said pair of bars.

12. A tennis ball tester according to claim 11, further including tension adjusting means coupled to said first spring.

13. A tennis ball tester according to claim 12, wherein said tension adjusting includes a tension adjusting screw extending through said housing for an adjustable connection to an end of said first spring remote from said one end of said other of said pair of bars.

14. A tennis ball tester according to claim 13, further including a roller connected to said one end of said other of said pair of bars adjacent said first spring engaging an inclined surface of said indicator arm between said second spring and said second pivot point to move said indicator arm in response to movement of said other of said pair of bars.

15. A tennis ball tester according to claim 14, further including a stop pin fastened to said housing adjacent said one end of said other of said pair of bars spaced from said first spring.

16. A tennis ball tester according to claim 15, wherein a portion of said force applying means extending out of said housing provides a first handle for said tennis ball tester.

17. A tennis ball tester according to claim 16, further including a second handle fastened to said housing opposite said portion of said force applying means.

18. A tennis ball tester according to claim 1, wherein said housing receives a plurality of tennis balls to be simultaneously tested.

19. A tennis ball tester according to claim 18, wherein said plurality of tennis balls number three.

20. A tennis ball tester according to claim 19, wherein said force applying means includes a threaded stud connected to said one of said pair of bars and extending outside of one end of said housing, and a knob secured to said threaded stud to enable turning said threaded stud to enable applying a force to said three tennis balls.

* * * * *